(12) United States Patent
Babapour

(10) Patent No.: US 7,060,729 B2
(45) Date of Patent: Jun. 13, 2006

(54) COMPOSITION AND METHOD FOR TREATING SKIN

(76) Inventor: Reza Babapour, 8670 Burton Way, #316, Los Angeles, CA (US) 90048

( * ) Notice: Subject to any disclaimer, the term of this patent is extended or adjusted under 35 U.S.C. 154(b) by 350 days.

(21) Appl. No.: 10/235,985

(22) Filed: Sep. 5, 2002

(65) Prior Publication Data

US 2004/0048914 A1  Mar. 11, 2004

(51) Int. Cl.
 *A61K 31/18* (2006.01)
 *A61K 31/44* (2006.01)
 *A61K 31/20* (2006.01)
(52) U.S. Cl. ............... 514/603; 514/298; 514/859; 514/558
(58) Field of Classification Search ............ 514/603, 514/398, 859, 558
 See application file for complete search history.

(56) References Cited

U.S. PATENT DOCUMENTS

| | | | |
|---|---|---|---|
| 5,543,417 | A | 8/1996 | Waldstreicher |
| 5,849,776 | A | 12/1998 | Czernielewski et al. |
| 5,972,993 | A | 10/1999 | Ptchelintsev |
| 6,126,947 | A | 10/2000 | Savion et al. |
| 6,153,208 | A | 11/2000 | McAtee et al. |
| 6,284,802 | B1 | 9/2001 | Bissett et al. |
| 2001/0034321 | A1 | 10/2001 | Herbert |
| 2002/0045667 | A1 | 4/2002 | Baker, Jr. et al. |
| 2002/0048798 | A1 | 4/2002 | Avery et al. |

OTHER PUBLICATIONS

Drug facts and comparisons(1997 edition), Azelaic acid(pp. 2848-2849) and metronidazole(pp. 2855-2856).*
Webster et al., Combination azelaic acid therapy for acne vulgaris., J Am Acad Dermatol., 2000; 43: s47-50.*
Jorizzo, Joseph L., et al., The efficacy of metronidazole 1% cream once daily compared with metronidazole 1% cream twice daily and their vehicles in rosacea: A double, blind clinical trial, Journal of the American Academy of Dermatology, vol. 39, No. 3, Sep. 1998, 1998, American Academy of Dermatology, Inc., USA.
Thiboutot, Diane M., Acne and Rosacea, New and Emerging Therapies, Dermatologic Clinics, vol. 18, No. 1, Jan. 2000, 2000 W.B. Saunders Company, USA.
Dahl, Mark V., et al., Topical Metronidazole Maintains Remissions of Rosacea, Archives of Dermatology, vol. 134(5), Jun. 1998, pp. 679-683, 1998, The American Medical Association, Chicago, IL, USA.
Wilkin, Jonathan K., Use of Topical Products for Maintaining Remission in rosacea, Archives of Dermatology, vol. 135(1), Jan. 1999, pp. 79-80, 1999, The American Medical Association, USA.
Dahl, Mark, V., et al , Once-daily topical metronidazole cream formulations in the treatment of the papules and postules of rosacea, Journal of the American Academy of Dermatology, vol. 45, No. 5, Nov. 2001, 20001 American Academy of Dermatology, Inc.
Mayr-Kanhauser, Sigrid, et al., Resolution of granulomatous rosacea after eradication of *Helicobacter pylori* with clarithromycin, metronidazole and pantoprazole, European Journal of Gastroenterology 2001 13:1379-1383, 2001, Lippincott Williams & Wilkins.
Utas, Serap, et al , *Helicobacter pylori* eradication treatment reduces the severity of rosacea, Journal of the American Academy of Dermatology, vol. 40, No. 3, Mar. 1999, 1999 American Academy of Dermatology, Inc., USA.
Shiotani, Akiko et al., Beneficial Effect of *Helicobacter pylori* Eradication in Dermatologic Diseases, Helicobacter, vol. 6, No. 1, 2001, Blackwell Science Ltd.
Bjerke, Roar, et al., Double-blind Comparison of Azelaic Acid 20% Cream and its Vehicle in Treatment of Papulo-Pustular Rosacea, Acta Derm Venerol 1999, 79:456-459, 1999, Scandinavian University Press.
Maddin, Stuart, A comparison of topical acid 20% cream and topical metronidazole 0.75% cream in the treatment of patients with papulopustular rosacea, Journal of the American Academy of Dermatology, vol. 40, No. 6, Jun. 1999, 1999, American Academy of Dermatology, Inc., USA.

* cited by examiner

*Primary Examiner*—Vickie Kim
(74) *Attorney, Agent, or Firm*—Canady & Lortz; Karen S. Canady

(57) ABSTRACT

The present invention relates to a composition and method for treating individuals afflicted with rosacea by combining a dicarboxylic acid, at least an antimicrobial agent, and a pharmaceutically acceptable carrier therefor into a topically applicable composition.

8 Claims, No Drawings

COMPOSITION AND METHOD FOR TREATING SKIN

FIELD OF THE INVENTION

The present invention relates generally to a composition and method for treating skin disorders and, more specifically, the present invention relates to the treatment of rosacea by the topical application of an effective amount of a formulation comprising metronidazole and azelaic acid.

BACKGROUND OF THE INVENTION

Several cosmetic and medical treatments have been used in an attempt to treat sensitive skin and related conditions in general, and rosacea in particular. The skin disorder rosacea is of an unknown origin. It usually affects the middle third of the face causing skin redness, prominent vascularization, papules, pustules and swelling, as well as a predisposition to flushing and blushing. However, Rosacea can also occur on other parts of the body including the chest, neck, back, or scalp. The blood vessels near the skin dilate and become more visible there through, resulting in telangiectasia. The resulting papules and pustules resemble teenage acne, and are frequently mistaken for the same. Unlike acne, rosacea does not have blackheads or whiteheads. Rosacea, however, can occur in all age groups and in both sexes, where it tends to be more frequent in women but more severe in men.

The flushing and blushing regions of the face are affected by rosacea. Emotional factors such as anxiety, embarrassment, or stress may evoke or aggravate rosacea. In addition, a flare-up may be caused by environmental or climate variances, and UV exposure is known to aggravate rosacea. Furthermore, diet is also known to aggravate rosacea. Spicy foods, alcoholic beverages, hot beverages, and smoking are known to cause flare-ups.

Rosacea is not only an aesthetic complication. Rosacea is a chronic disease that has rarely been documented to reverse its progression. If untreated, the condition worsens and spreads. Untreated rosacea may cause a disfiguring nose condition called rhinophyma, which is characterized by a bulbous, red nose and inflamed cheeks. Severe rhinophyma may require surgery, an invasive procedure that may be avoided by timely treatment. Another problem of advanced rosacea is ocular. Persons afflicted with rosacea may experience conjunctivitis, a burning and grittiness of the eyes. If untreated, it may lead to serious complications such as rosacea keratitis, which damages the cornea and may impair vision.

Even though the exact origin of rosacea is unknown, several hypotheses have been offered. Many possible causes have been described as inducing the disease or contributing to its manifestation, including psychogenic, pharmacological, alimentary, thermal, infectious and immunological. It is also been claimed that Demodex mites may also cause the disease. Furthermore, the bacteria *Helicobacter pylori*, which is an important cause of gastritis and gastric and duodenal ulcers, has been reported as a possible cause for various dermatological disorders. The frequent association of rosacea with gastrointestinal tract disorders suggests a possible involvement of *H. pylori* in the cause of the skin disorder (Shiotani, A., *Helicobacter*, 6:60–65 (2001)).

As a result of the hypotheses as to the cause of rosacea, several treatments for the condition have been based thereon. Based upon the association of rosacea and *H. pylori*, antibiotics that are effective against *H. pylori* have also been used to successfully treat rosacea. Antibiotics, such as clarithromycin, tetracyclines, pantoprazole, and metronidazole, have proven to be effective in eliminating *H. pylori*, and in some cases rosacea (Mayr-Kanhauser, S. et al., European Journal of Gastroenterology & Hepatology, 13:1379–83 (2001)). In addition, combinations of antibiotics administered to patients having *H. pylori* and rosacea have proven to be effective in treating rosacea. The administration of a combination of amoxicillin, metronidazole, and bismuth subcitrate, to *H. pylori* positive patients has proven effective in decreasing the severity of rosacea, wherein the lesions were improved by the eradication of *H. pylori* (Utas, S. et al., Journal of the American Academy of Dermatology, 40:433–35 (1999)).

Metronidazole has demonstrated to be efficacious in treating rosacea. Twice-daily applications of the 0.75% metronidazole cream and a once-daily regimen of 1.0% metronidazole cream have found no significant difference in their effectiveness, but the once-daily regimen is best for patient compliance (Dahl, M. et al., Journal of the American Academy of Dermatology, 45:723–30 (2001)). However, it has also been noticed that patients treated with tetracycline and topical metronidazole, have had relapses in approximately twenty-five percent of cases in one case study (Thiboutot, D., Dermatologic Clinics, 18:63–71 (2000)). In addition, U.S. Pat. No. 5,849,776 to Czernielewski et al. teaches the effectiveness of Metronidazole, either individually or in combination with clindamycin, in the treatment of the papules and pustules of rosacea.

U.S. Pat. No. 5,972,993 to Ptchelinstev, assigned to Avon Products, Inc. ('993 patent), states that metronidazole has been shown to have an effect on papules and pustules of rosacea, but has been reported to be ineffective against skin redness, telangiectasia or flushing. Accordingly, the '993 patent teaches a composition having free radical scavengers, that is antioxidants, for the treatment of rosacea. Although the teachings may be effective against redness, telangiectasias, and flushing, the antioxidants do not address the papules and pustules caused by rosacea.

U.S. Pat. No. 6,126,947 to Savion et al. teaches a method for treatment of skin disorders, including rosacea, by topical application of an inhibitor of cholesterol synthesis. While inhibitors of cholesterol synthesis were previously administered orally or parenterally for lowering the cholesterol level of the patient they were never formulated as a topical composition. The extent of information available regarding its effectiveness in the treatment of the various aspects of rosacea is minimal and it only addresses the elimination of redness and not the effectiveness against the papules and pustules.

U.S. Pat. No. 6,284,802 to Bissett et al. ('802 patent) discloses the use of farnesol in a topical composition for the treatment of keratinous tissue. Although the '802 patent discusses rosacea as a possible skin disorder that may be treated by the farnesol composition, it does not provide any test results in support of the same.

U.S. Patent Application Pub. No. 2001/0034321 to Hebert discloses water-soluble salts of azelaic acid wherein the azelaic acid is combined with chitosan and administered to a subject. The Application fails to provide any concrete treatment of rosacea with the composition and merely mentions rosacea as a skin disorder that may be effectively treated by the taught composition.

An alternate study involving azelaic acid has shown that topical application thereof has beneficial effects in treating rosacea. Azelaic acid, a naturally occurring dicarboxylic acid, was first used in the treatment of acne and hyperpigmentation before being applied to rosacea. Topical application of azelaic acid has been shown to significantly reduce inflammatory papule lesions and erythema. However, the azelaic acid treatment did not produce any major improvement in telangiectasia. In addition, azelaic acid was not effective in treating pustules caused by rosacea (Bjerke, R. et al., *Acta Derm Venereol,* 79:456–59 (1999)).

Another study has reported the efficacy of metronidazole when compared with azelaic acid. Results of the treatments demonstrate that both medications are equally effective in reducing the number of inflammatory lesions and associated signs and symptoms of rosacea. However, the physicians administering the medications rated the global improvement of the patients more favorably for azelaic acid than metronidazole. It was determined that although both medications were effective in treating erythema, dryness, and burning associated with rosacea, both medications failed to effect telangiectasia. As a result, the study concluded that azelaic acid provides a very effective alternative to metronidazole cream even though neither compound is effective in addressing telangiectasia (Maddin, S., *Journal of the American Academy of Dermatology,* 40:961–65 (1999)).

Other current therapies for rosacea have had some drawbacks. Topically administered erythromycin and clindamycin, or similar antibiotics, are not tolerated for long term use because of the side effects associated therewith, such as gastrointestinal irritation. Topical corticosteroids have been effective in treating inflammation associated with rosacea, however long-term use thereof has resulted in skin atrophogenia. Isotretinoin has been shown to ameliorate rosacea and lasers can be used to treat telangiectasia. However, because of the chronic nature of rosacea, the ideal treatment needs to be used long-term in a safe and convenient manner.

Thus, a need exists for a composition and method for treating rosacea without causing the undesirable side effects of the prior art. In addition, a need exists for a composition and method for treating rosacea that is more effective. Furthermore, a need exists for a composition and method for stabilizing telangiectasia. The present invention satisfies these needs and provides related advantages as well.

SUMMARY OF THE INVENTION

Accordingly, the primary objective of the present invention is to overcome the limitations of the prior art.

Another object of the invention is to provide methods for treating individuals afflicted with rosacea.

It is another object of the present invention to provide a pharmaceutical composition comprising a pharmaceutically acceptable carrier effective in treating rosacea.

It is another object of the present invention to provide a method for administering such a composition to an affected region.

It is a further object of the present invention to provide a novel composition and method for treating rosacea.

It is another object of the present invention to provide a more effective composition and method for treating rosacea.

It is a further object of the present invention to provide a composition and method for treating not only the redness, flushing and blushing that is associated with rosacea, but is also effective in treating the pustules and papules caused thereby.

It is yet a further object of the present invention to provide a composition and method for stabilizing telangiectasia associated with rosacea.

In brief, such stated objects and advantages of the invention are achieved by the application, in combination, of currently available azelaic acid and metronidazole. In one preferred embodiment, a composition comprising equal parts of azelaic acid and metronidazole is applied twice daily to the area of the skin afflicted with rosacea. With the composition and method of the instant invention, augmented effectiveness has been observed in the treatment of rosacea.

Such stated objects and advantages of the invention are only examples and should not be construed as limiting the present invention. These and other objects, features, aspects, and advantages of the invention herein will become more apparent from the following detailed description of the embodiments of the invention when taken in conjunction with the accompanying figures and the claims that follow.

DETAILED DESCRIPTION OF THE PREFERRED EMBODIMENTS

The instant invention relates to a composition and method for treating skin disorders in general and rosacea specifically. Although the present invention discloses a preferred method of treating rosacea by the topical application of the present composition, it is to be understood that the instant invention is not limited thereby and that a combination of applications, i.e. oral or topical, may also be used without departing from the essence of the instant invention as claimed. Topical application as used herein means to apply to the surface of the skin affected by the ailment, e.g. rosacea.

The percentages and ratios used hereinafter are by weight of the total composition unless specifically designated otherwise. The composition of the present invention comprises metronidazole and azelaic acid, however, the composition may also include additional ingredients that do not alter the effectiveness of the combination and do not depart from the essence of the instant invention and, may in fact, augment the effectiveness of the composition of the essential ingredients.

The term "effective amount" is to be understood as meaning an amount of an active ingredient needed to achieve a desired therapeutic or cosmetic effect. For example, in a pharmaceutical composition of the invention an effective amount the composition comprising metronidazole and azelaic acid is an amount that is sufficient to achieve an improvement in the skin's condition. In a cosmetic composition, an effective amount is an amount that causes an improvement in the skin appearance.

Chemically, metronidazole is 2-methyl-5-nitro-1H-imidazole-1-ethanol. The molecular formula for metronidazole is $C_6H_9N_3O_3$. It has the following structural formula:

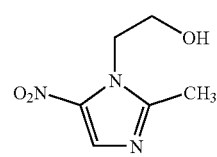

The term "metronidazole" as used in this specification and claims is meant to include not only 2-methyl-5-nitro-1H-imidazole-1-ethanol, but also those analogs and derivatives of metronidazole which are solubilized in the liquid compositions described herein and which have therapeutic activity when topically applied. Metronidazole is employed in the compositions in a therapeutically effective amount. The actual concentration of metronidazole may vary, depending on the nature and degree of the disorders being treated, and whether the drug is being administered for therapeutic or prophylatic purposes. The compositions advantageously comprise at least about 0.1 wt-% metronidazole, based on the total weight of the composition. Preferably metronidazole is present in an amount of about 0.25% to about 1.0%, and more preferably about 0.75% by weight, based on the total weight of the composition. For purposes of illustration, and not limitation, in the example detailed hereinafter, the metronidazole used was obtained from Galderma Laboratories, Inc. located in Fort Worth, Tex. and is sole under the trademark METROGEL®. The concentration of metronidazole in the METROGEL® is 0.75%.

Chemically, azelaic acid is 1,7-heptanedicarboxylic acid. The molecular formula for azelaic acid is $C_9H_{16}O_4$. It has the following structural formula:

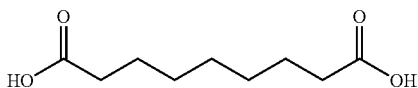

Azelaic acid is a saturated aliphatic $C_9$ dicarboxylic acid which is also known as nonanedioic acid or heptane dicarboxylic acid. Dicarboxylic acids of primary interest in accordance with this invention are those having 7 to 13 carbon atoms, with those having 8 to 12 carbon atoms preferred. This includes both straight-chain and branched-chain compounds, both saturated and unsaturated (i.e., having one or more double bonds).

Accordingly, it is to be understood that the specific tests conducted using azelaic acid described herein do not limit the composition to azelaic acid alone. Other dicarboxylic acids may be substituted for azelaic acid without departing the essence of the present invention as long as the active ingredients of the composition are not negatively affected. For purposes of illustration, and not limitation, in the example detailed hereinafter, the azelaic acid used was obtained from Allergan, Inc., located in Irvine, Calif. and is sole under the trademark AZELEX®. The concentration of azelaic acid in the AZELEX® is 20%.

The therapeutic effectiveness of the instant compositions of the present invention is demonstrated in the following examples. These examples are meant to illustrate the invention rather than to limit its scope. Variations in the compositions which do not adversely affect the effectiveness of metronidazole and azelaic acid will be evident to one skilled in the art, and are within the scope of this invention. For example, additional ingredients such as coloring agents, sunscreens, and the like may be included in the compositions as long as the resulting composition retains the desirable properties, e.g., non-comedogenicity, high specific activity, and the like, described above.

In addition, the present invention relates to pharmaceutical compositions comprising a pharmaceutically acceptable carrier and the active ingredients of the instant invention. It is believed that the effect of the present active ingredients will be synergistically improved when combined with a humectant, an emollient or an antiinflammatory.

The addition of humectants and emollients to the active ingredients is expected to aid in the rehydration and maintenance of hydration of the treated skin. Improved hydration of the skin is believed to both increase the absorbance of the active ingredients by the skin and augment the delivery of the active ingredients to the afflicted site.

It is contemplated that conventional emollients known in the art may also be added to the composition. Examples of these emollients are: mineral oil, petrolatum, paraffin, ceresin, ozokerite, microcrystalline wax, perhydrosqualene dimethyl polysiloxanes, methylphenyl polysiloxanes, silicone, silicone-glycol copolymers, triglyceride esters, acetylated monoglycerides, ethoxylated glycerides, alkyl esters of fatty acids, fatty acids and alcohols, lanolin and lanolin derivatives, polyhydric alcohol esters, sterols, beeswax derivatives, polyhydric alcohols and polyethers, and amides of fatty acids. Other suitable emollients can be found in the prior art and are incorporated herein by reference.

Humectants known in the art to increase skin hydration when applied topically, such as polyhydric alcohols may also be added to the composition. Examples of suitable humectants are: glycerin, propylene glycol, butylene glycol, diglycerol, or ester derivatives thereof. However, the preferred humectant is glycerin.

Any antiinflammatory known in the art to be suitable for topical application would be appropriate for use in the present invention. It is believed that the addition of an antiinflammatory will also increase absorbency and facilitate delivery of the active ingredients to the active site. The antiinflammatories contemplated for combination with the antioxidant can be either steroidal or non-steroidal. Steroidal antiinflammatories are preferred for more severe cases of rosacea. Non-steroidal antiinflammatories are preferred for less severe cases of rosacea. The preferred antiinflammatories are those antiinflammatories that inhibit enzymes involved in inflammatory cascades. Most preferred are antiinflammatories that inhibit lipoxygenase. It is believed that it is the products of lipoxygenase action that are of primary importance in skin inflammation. In addition, it is believed that antiinflammatories that function by inhibiting platelet aggregating factors will also produce synergistic results when combined with the instant composition. Examples of preferred antiinflammatories are hydrocortisone, boswellic acid or extracts of Boswellia serrata, indomethacin, salicylic acid, acetyl salicylic acid and other salicylic acid derivatives. The more preferred of these antiinflammatories are boswellic acid and salicylic acid derivatives since these antiinflammatories are known to have excellent compatibility with the skin.

Antimicrobial agents are pharmacological agents useful for the treatment of dermatological disorders. However, compositions comprising dermatologically effective amounts of a combination of antimicrobial agents and the active ingredients of the instant invention are not available. Additionally, compositions comprising dermatologically effective amounts of a combination of sulfacetamide or a salt thereof, such as sodium sulfacetamide, with metronidazole and azelaic acid are not currently available. The desired amount of active ingredient can vary from composition to composition depending on the particular disorder or disorders being treated, the severity of the disorder, the duration of the treatment, the other specific components of the composition being used, and like factors.

In one embodiment, the antimicrobial agent can be present in the composition at a concentration from about 0.001% to about 20% by weight. In another embodiment, the antimicrobial agent can be present at a concentration of about 10% by weight. One or more antimicrobial agents can be included in the compositions of the invention. As used herein, "antimicrobial agent" means an agent that can inhibit the growth of a microorganism or kill a microorganism. Antimicrobial agents can have microbial-static effects and/or microbial-cidal effects. Antimicrobial agents can be synthetic compounds, semisynthetic compounds, and naturally produced compounds. As used herein, "antimicrobial agent" refers to both an antimicrobial agent compound and salts thereof. Preferably the antimicrobial agents are dermatologically absorbable. Suitable dermatologically absorbable antimicrobial agents include erythromycin, bacitracin, zinc bacitracin, polymycin, neomycin, chloramphenicol, tetracycline, sulfacetamide, minocycline, clindamycin, doxycycline, undecylenic acid and salts thereof, propionic acid and salts thereof, caprylic acid and salts thereof, ciprofloxacin, cephlasporins, benzoic acid, ciclopiroxolamine, clotrimazole, econazole nitrate, metronidazole, miconazole nitrate, ketacanazole, oxiconazole, tolnaftate. However, in the preferred embodiment of the present composition, sodium sulfacetamide lotion may be used at a concentration of either 5% or 10%. The sodium sulfacetamide lotion may be obtained from Dermik Laboratories, Collegeville, Pa. sold as "SULFACET LOTION."

EXAMPLE I

The aim of this example is for purposes of illustration and not limitation. This example demonstrates the effectiveness of the in vivo topical application of a composition comprising 20% azelaic acid and 0.75% of metronidazole. The composition was topically applied to one patient afflicted with rosacea twice daily for a period of four to six weeks. The patient did not complain of burning or irritation. The patient returned to the clinic after having used the cream for four to six weeks for a visual inspection of the afflicted area of the face.

The examining physician noted that the patient's rosacea had improved by the combination of the active ingredients of the instant composition. The rosacea had also improved in a shorter duration by the application of the combination of the active ingredients of the instant composition when compared to other patients using the active ingredients separately. A marked decrease in erythema and inflammation was also observed. Talengectasia was also stabilized in the patient. Overall, the instant composition augmented the effectiveness of the active ingredients in treating rosacea when compared to the application of the active ingredients alone.

While there are specific concentrations of agents set forth above, it is to be understood that varying concentrations of the agents can also be used. Therefore, the invention is not limited by the specific concentrations listed above. Furthermore, it is to be understood that analogues of the present compounds that are known in the art to have similar functions, may also be used in combination with the active ingredients listed above to augment the effectiveness thereof.

While the above description contains many specificities, these should not be construed as limitations on the scope of the invention, but rather as an exemplification of preferred embodiments thereof. Many other variations are possible without departing from the essential spirit of this invention. Accordingly, the scope of the invention should be determined not by the embodiment illustrated, but by the claims and their legal equivalents.

What is claimed is:

1. A composition for treating rosacea or flushing and/or blushing associated therewith, the composition consisting essentially of:
    a dicarboxylic acid, wherein the dicarboxylic acid comprises 10–30% by weight azelaic acid;
    a first antimicrobial agent, wherein the first antimicrobial agent comprises 0.25–1% by weight metronidazole;
    sulfacetamide; and
    a pharmaceutically acceptable carrier thereof.

2. The composition of claim 1, wherein said metronidazole is present in about 0.75% by weight and said azelaic acid is present in about 20% by weight.

3. The composition of claim 1, wherein said sulfacetamide is sodium sulfacetamide.

4. A composition for treating rosacea or flushing and/or blushing associated therewith consisting essentially of:
    20% by weight azelaic acid;
    0.75% by weight metronidazole;
    sulfacetamide; and
    a pharmaceutically acceptable carrier thereof.

5. The composition of claim 4, wherein said metronidazole is present in about 0.75% by weight and said azelaic acid is present in about 20% by weight.

6. The composition of claim 4, wherein said sulfacetamide is sodium sulfacetamide.

7. A method for treating rosacea or flushing and/or blushing associated therewith comprising:
    applying topically to an individual in need thereof the composition of claim 1.

8. A method for treating rosacea or flushing and/or blushing associated therewith comprising:
    applying topically to an individual in need thereof the composition of claim 4.

* * * * *